United States Patent [19]

Kühle et al.

[11] Patent Number: 4,764,433

[45] Date of Patent: Aug. 16, 1988

[54] AGENT FOR THE PROTECTION OF MATERIALS

[75] Inventors: Engelbert Kühle, Bergisch-Gladbach; Wilfried Paulus, Krefeld; Michael Fischler, Krefeld; Hans-Georg Schmitt, Krefeld, all of Fed. Rep. of Germany

[73] Assignee: Bayer Aktiengesellschaft, Leverkusen, Fed. Rep. of Germany

[21] Appl. No.: 897,001

[22] Filed: Aug. 15, 1986

[30] Foreign Application Priority Data

Sep. 3, 1985 [DE] Fed. Rep. of Germany ....... 3531363

[51] Int. Cl.$^4$ .......................... B32B 9/04; C09D 5/16
[52] U.S. Cl. .................. 428/541; 106/18.32; 428/15; 428/245; 428/447; 564/87
[58] Field of Search ............ 428/15, 245, 447, 537.1, 428/537.5, 541; 106/18.32; 564/87

[56] References Cited

U.S. PATENT DOCUMENTS

| | | | |
|---|---|---|---|
| 3,285,929 | 11/1966 | Klauke et al. | 548/210 |
| 3,341,403 | 9/1967 | Klauke et al. | 514/372 |
| 3,386,951 | 6/1968 | Pauli et al. | 523/122 |
| 4,337,093 | 6/1982 | Metzner et al. | 106/18.33 |
| 4,402,980 | 9/1983 | Kuhle et al. | 564/79 |

FOREIGN PATENT DOCUMENTS

| | | |
|---|---|---|
| 27622 | 10/1980 | European Pat. Off. . |
| 1193498 | 5/1965 | Fed. Rep. of Germany . |
| 1238139 | 4/1967 | Fed. Rep. of Germany . |
| 22900 | 3/1980 | Fed. Rep. of Germany . |
| 3137061 | 3/1983 | Fed. Rep. of Germany ........ 564/87 |
| 3313718 | 10/1984 | Fed. Rep. of Germany ........ 564/87 |
| 716553 | 10/1954 | United Kingdom . |
| 994603 | 6/1965 | United Kingdom .................. 564/87 |

*Primary Examiner*—Theodore Morris
*Attorney, Agent, or Firm*—Sprung Horn Kramer & Woods

[57] ABSTRACT

An agent for the protection of material containing an N-sulphenylated benzenesulphonamide of the formula

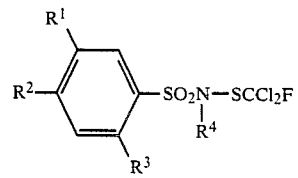

wherein
$R^1$, and $R^2$ and $R^3$ independently of one another represent hydrogen, halogen, nitro, alkyl or halogenoalkyl and
$R^4$ denotes an unsubstituted or substituted, saturated or unsaturated, aliphatic or cycloaliphatic radical, the aliphatic radicals being uninterrupted or heteroatoms or being interrupted by one or more hetero-atoms. The N-sulphenylated benzenesulphonamide-containing agents are useful for protecting industrial materials, for example, paints and timber, against attack by microorganisms, such as bacteria, fungi, yeasts, algae, slimes and viruses.

13 Claims, No Drawings

AGENT FOR THE PROTECTION OF MATERIALS

BACKGROUND OF THE INVENTION

1. Field of the Invention

The invention relates to an agent, containing N-sulphenylated benzenesulphonamides, for the protection of materials.

2. Background Information

The use of N-fluorodichloromethylthio compounds in the protection of materials, for example as industrial preservatives, is disclosed in DE-AS (German Published Specification) No. 1,238,139, in *Angew. Chem.*, 76, page 807 (1964) and in *Holz als Roh- und Werk-stoff*, 35, (1977) 233 to 237. Although the N-fluorodichloromethylthio compounds disclosed in the publications mentioned, such as N,N-dimethyl-N'-phenyl-N'-(fluorodichloromethylthio)-sulphamide (dichlofluanid), N-fluorodichloromethylthiophthalimide (fluorfolpet), 1,3-(bisdichlorofluoromethylthio)-benzimidazolone and N,N-dimethyl-N'-(4-tolyl)-N'-(fluorodichloromethylthio)-sulphamide, are suitable for use in the protection of materials by virtue of their microbicidal action, they do not always give satisfaction in their mode of action, for example in timber preservatives. Thus, for example, dichlofluanid, mentioned above, has the disadvantage that it is very sparingly soluble in the formulating agents customary for timber preservatives, which results in large amounts being required for formulation in order to apply the required amount of active compound to and/or in the timber.

The use of N-fluorodichloromethylthio compounds, such as the use of N-sulphenylated benzenesulphonamides (see appropriate formula in Example 4), in plant protection agents having a fungicidal action is also disclosed in DE-AS (German Published Specification) No. 1,193,498.

SUMMARY OF THE INVENTION

The present invention relates to an agent, for the protection of materials, containing N-sulphenylated benzenesulphonamides of the formula

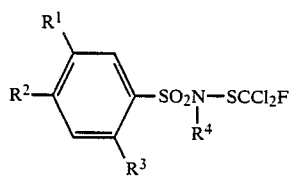

wherein $R^1$, $R^2$ and $R^3$ independently of one another represent hydrogen, halogen, nitro, alkyl or halogenoalkyl and $R^4$ denotes an optionally substituted, saturated or unsaturated, aliphatic or cycloaliphatic radical, it being possible for the aliphatic radicals to be optionally interrupted one or more times by hetero-atoms.

The invention also relates to the use of the N-sulphenylated benzenesulphonamides of the above-mentioned formula for the protection of industrial materials.

DETAILED DESCRIPTION OF THE INVENTION

Preferred N-sulphenylated benzenesulphonamides of the formula mentioned are those in which $R^1$, $R^2$ and $R^3$ independently of one another represent hydrogen, chlorine, bromine, nitro, alkyl having 1 to 4C atoms, or halogenoalkyl having 1 to 4C atoms and 1 to 5 halogen atoms and $R^4$ represents alkyl having 1 to 6C atoms, or alkenyl and alkinyl having 3 to 6C atoms, it being possible for these radicals to be optionally interrupted one or more times (preferably once) by hetero-atoms, such as oxygen or sulphur, or to be substituted by halogen, such as chlorine or iodine, or $R^4$ represents cycloalkyl having 3 to 7 ring C atoms which can optionally be substituted by one or more (preferably 1 to 3) lower alkyl radicals having 1 to 3C atoms.

N-Sulphenylated benzenesulphonamides of the above-mentioned formula which are particularly preferred are those in which $R^1$ and $R^2$ independently of one another represent hydrogen, chlorine, nitro, methyl and trifluoromethyl, $R^3$ represents hydrogen and $R^4$ represents alkyl having 1 to 6C atoms, or alkenyl and alkinyl having 3 to 6C atoms, which can optionally be interrupted one or more times (preferably once), starting from the second C atom, by hetero-atoms, such as oxygen or sulphur, or can be substituted by iodine, or $R^4$ represents cycloalkyl having 3 to 7 ring C atoms which can optionally be substituted by one or more (preferably 1 to 3) methyl radicals.

The following N-sulphenylated benzenesulphonamides of the formula below should be mentioned individually:

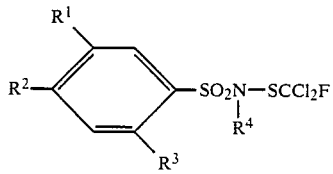

| $R^1$ | $R^2$ | $R^3$ | $R^4$ |
|---|---|---|---|
| H | H | H | $C_2H_5$ |
| H | H | H | $C_3H_7$—iso |
| H | H | H | $C_4H_9$—iso |
| H | H | H | $C_4H_9$—tert. |
| H | H | H | $CH_2C(CH_3)_3$ |
| H | Cl | H | $C_3H_7$ |
| H | Cl | H | $C_3H_7$—iso |
| H | Cl | H | $CH_2CH=CH_2$ |
| Cl | H | H | $CH_3$ |
| Cl | H | H | 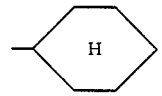 |
| H | $CH_3$ | H | $CH_3$ |
| H | $CH_3$ | H | $C_4H_9$—n |
| H | $CH_3$ | H | 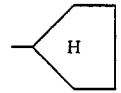 |
| H | $CH_3$ | H | 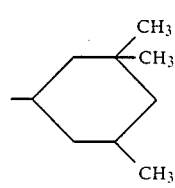 |
| H | $CF_3$ | H | $CH_3$ |
| H | $CF_3$ | H | $C_2H_5$ |

-continued $$R^2 \underset{R^3}{\overset{R^1}{\diagdown}} \text{—SO}_2\text{N—SCCl}_2\text{F}$$
$$\qquad\qquad\qquad\qquad |$$
$$\qquad\qquad\qquad\qquad R^4$$

| $R^1$ | $R^2$ | $R^3$ | $R^4$ |
|---|---|---|---|
| $NO_2$ | H | H | $CH_3$ |
| H | $NO_2$ | H | $CH_3$ |
| H | $NO_2$ | H | –⟨H⟩–$CH_3$ |
| $NO_2$ | H | $CH_3$ | $CH_3$ |
| $NO_2$ | H | $CH_3$ | $CH_2CH=CH_2$ |
| $NO_2$ | H | $CH_3$ | iso-$C_4H_9$ |
| $NO_2$ | H | $CH_3$ | $CH_2CH_2CH_2OCH_3$ |
| H | H | $NO_2$ | $C_2H_5$ |
| H | H | $NO_2$ | $CH_2$–C($CH_3$)$_3$ |
| $NO_2$ | H | Cl | $CH_2CH_2SC_2H_5$ |
| $NO_2$ | H | Cl | $C_3H_3$ |
| H | H | $CH_3$ | $CH_3$ |
| H | H | $CH_3$ | n-$C_3H_7$ |
| H | H | $CH_3$ | n-$C_4H_9$ |
| Cl | Cl | H | $CH_3$ |
| Cl | Cl | H | iso-$C_3H_7$ |
| H | H | H | $CH_2C\equiv Cl$ |
| Cl | Cl | H | $CH_2C\equiv Cl$ |
| Preferred: | | | |
| H | H | H | $C_2H_5$ |
| $CH_3$ | $CH_3$ | H | $CH_3$ |
| H | $CH_3$ | H | $C_2H_5$ |
| H | $CH_3$ | H | $C_4H_9$ |
| H | Cl | H | $C_4H_9$ |
| $NO_2$ | $CH_3$ | H | $CH_3$ |
| $NO_2$ | $CH_3$ | H | $C_4H_9$ |
| $NO_2$ | H | H | $CH_3$ |
| $NO_2$ | H | H | $C_4H_9$ |
| H | $CH_3$ | H | $C_6H_{11}$ |
| H | $CH_3$ | H | $C_3H_5$ |
| H | $CH_3$ | H | $CH_3$ |
| H | Cl | H | $C_2H_5$ |
| H | $NO_2$ | H | $CH_3$ |
| Particularly preferred: | | | |
| H | $CH_3$ | H | $CH_3$ |
| H | $CH_3$ | H | $C_2H_5$ |
| H | Cl | H | $C_2H_5$ |
| $NO_2$ | $CH_3$ | H | $CH_3$ |
| H | $NO_2$ | H | $CH_3$ |
| H | H | H | $C_2H_5$ |
| $CH_3$ | $CH_3$ | H | $CH_3$ |

Examples of industrial materials within the scope of the invention and which can be protected against microbial change and destruction by means of the N-sulphenylated benzenesulphonamides (described as active compounds) of the formula mentioned are adhesives, glues, paper and cardboard, textiles, leather, timber, paints, silicone rubbers and plastics articles, in particular paints and timber which have been prepared for use in industry.

Examples of microorganisms which can cause degradation or change in industrial materials are bacteria, fungi, yeasts, algae and slimes. The substances according to the invention are preferably effective against mold fungi, fungi which discolor timber and fungi which destroy timer (basidomycetes) and against slime organisms.

Microorganisms of the following genera may be mentioned as examples:

alternaria, such as *Alternaria tenuis*, aspergillus, such as *Aspergillus niger*, chaetomium, such as *Chaetomium globosum*, coniophora, such as *Coniophora puteana*, lentinus, such as *Lentinus tigrinus*, penicillium, such as *Penicillium glaucum*, polyporus, such as *Polyporus versicolor*, aureobasidium, such as *Aureobasidium pullulans*, sclerophoma, such as *Sclerophoma pityophila* and staphylococcus, such as *Staphylococcus aureus*.

The N-sulphenylated benzenesulphonamides of the abovementioned formula can be converted, depending on the fields of use, into the customary formulations, such as solutions, emulsions, suspensions, powders, pastes, granules, foams and aerosols.

Concentrations for use of the active compounds according to the invention depend on the nature and occurrence of the microorganisms to be combated, and on the composition of the material to be protected. The optimum amount to be employed can be determined by a series of tests. In general, the concentrations for use are within the range from 0.001 to 5% by weight, preferably 0.05 to 1.0% by weight, relative to the material to be protected.

The agent, according to the invention, for the protection of materials contains an amount of about 1 to 95% by weight, preferably 10 to 90% by weight, of the N-sulphenylated benzenesulphonamide.

The active compounds according to the invention can also be in the form of a mixture with other known active compounds. The following active compounds may be mentioned as examples: benzyl alcohol mono(-poly)hemiformal and other compounds which split off formaldehyde, benzimidazolyl-methylcarbmates, tetramethylthiuram disulphide, zinc salts of dialkyldithiocarbamates, 2,4,5,6-tetrachloroisophthalonitrile, thiazolylbenzimidazole, mercaptobenzthiazole, 2-thiocyanatomethylthiobenzthiazole, organotin compounds, methylene bisthiocyanate, phenol derivatives, such as 2-phenylphenol, (2,2'-dihydroxy-5,5'-dichloro)-diphenylmethane and 3-methyl-4-chlorophenol, and other N-trihalogenomethylthio compounds, such as folpet, fluorfolpet and dichlofluanid.

Although the use of some N-sulphenylated benzenesulphonamides as plant protection agents having a fungicidal action is disclosed in DE-AS (German Published Specification) No. 1,193,498 (see the appropriate formula in Example 4), it is nevertheless extremely surprising that the N sulphenylated benzenesulphonamides, according to the invention, of the formula mentioned above are particularly effective microbicides for agents for the protection of materials. As shown in the comparison example below and the comparison table (in this regard see the example section), the N-sulphenylated sulphamides disclosed as agents for the protection of materials in DE-AS (German Published Specification) No. 1,238,139, such as N,N-dimethyl-N'-phenyl-N'-dichlorofluoromethylthiosulphamide (dichlofluanid) and N,N-dimethyl-N'-(4-tolyl)-N'-dichlorofluoromethylthio-sulphamide, possess considerably better fungicidal properties for plant protection (phytophthora test [tomatoes]) than the N-sulphenylated benzenesulphonamides according to the invention. On the basis of their poorer fungicidal properties for plant protection it would, therefore, have been expected that the N-sulphenylated benzenesulphonamides according to the invention would also have poorer antimicrobial properties for the protection of materials than the sulphamides which are disclosed in DE-AS (German Published Specification) No. 1,238,139 and are used in the protection of materials.

It will be appreciated that the instant specification and claims are set forth by way of illustration and not limitation, and that various modifications and changes may be made without departing from the spirit and scope of the present invention.

I. PREPARATION EXAMPLES

Example 1

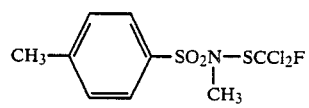

18.5 g (0.1 mol) of 4-toluenesulphonic acid N-methylamide are dissolved in 100 ml of toluene, with the addition of 16.9 g (0.1 mol) of dichlorofluoromethane-sulphenyl chloride, and a solution of 11.2 g (0.11 mol) of triethylamine in 20 ml of toluene is added at room temperature. In the course of this the temperature rises to about 50° C. Water is added, the layers are separated and the toluene solution is dried and concentrated in vacuo. The residue (27 g; $n_d^{20}$ 1.5519, yield 21 g=66% of theory, melting point; 42°–43° C. is the N-fluorodichloromethylthio-N-methylamide of 4-toluenesulphonic acid.

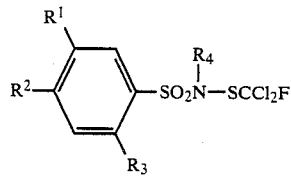

is obtained analogously.

| Example | $R^1$ | $R^2$ | $R^3$ | $R^4$ | Melting point ($n_D^{20}$; boiling point) |
|---|---|---|---|---|---|
| 2 | H | H | H | $C_2H_5$ | (133–40°/0.2) |
| 3 | H | H | H | $C_4H_9$-n | (140–45°/0.1) |
| 4 | H | $CH_3$ | H | $C_2H_5$ | (153–58°/0.2) |
| 5 | H | $CH_3$ | H | $C_4H_9$ | (168–69°/0.15) |
| 6 | H | Cl | H | $C_2H_5$ | (170–75°/0.2) |
| 7 | H | Cl | H | $C_4H_9$ | (170–75°/0.15) |
| 8 | $NO_2$ | $CH_3$ | H | $CH_3$ | 69–70° |
| 9 | $NO_2$ | $CH_3$ | H | $C_4H_9$ | 56–58° |
| 10 | $NO_2$ | H | $CH_3$ | $C_4H_9$ | 86–88° |
| 11 | H | H | $NO_2$ | $C_4H_9$ | 76–78° |
| 12 | $NO_2$ | H | H | $C_4H_9$ | 62° |
| 13 | $NO_2$ | Cl | H | $C_4H_9$ | 74–75° |
| 14 | H | $NO_2$ | H | $CH_3$ | 107–108° |
| 15 | H | $NO_2$ | H | $C_4H_9$ | (1.5574) |
| 16 | $NO_2$ | H | Cl | $C_4H_9$ | 57–58° |
| 17 | $CH_3$ | $CH_3$ | H | $CH_3$ | Cl calculated 21.4 found 21.4 |
| 18 | $CH_3$ | $CH_3$ | H | $C_3H_7$-iso | 78–80° |
| 19 | $CH_3$ | H | $CH_3$ | $CH_3$ | 79° |

-continued

| Example | $R^1$ | $R^2$ | $R^3$ | $R^4$ | Melting point ($n_D^{20}$; boiling point) |
|---|---|---|---|---|---|
| 20 | H | $CH_3$ | H | $C_6H_{11}$ | 89–90° |
| 21 | H | $CH_3$ | H | $C_3H_5$ | (1.5536) |
| 22 | H | $CH_3$ | H | $CH_2CH_2CH_2OCH_3$ | (1.5396) |
| 23 | H | $CH_3$ | H | $C_5H_9$ | (1.5683) |
| 24 | H | H | H | $CH_3$ | (140–45°/0.12) |
| 25 | Cl | Cl | H | $CH_3$ | 68–69° |
| 26 | $NO_2$ | Cl | H | $CH_3$ | 94–95° |
| 27 | $NO_2$ | H | H | $CH_3$ | 69–70° |
| 28 | Cl | H | Cl | $CH_3$ | 89–92° |
| 29 | H | Cl | H | $C_4H_9$ | (170–75°/0.15) |

N-Dichlorofluoromethylsulphenyl-N-iodopropargyl-benzenesulphonamides 0.1 mol of an N-iodopropargylbenzenesulphonamide is dissolved in THF, 18.6 g (0.11 mol) of dichlorofluoromethanesulphenyl chloride are added, and the solution is cooled to 0° C. 11 g (0.11 mol) of triethylamine are added dropwise slowly at this temperature. The mixture is allowed to reach room temperature slowly and is then heated at 60° C. for 1 hour. The solvent is removed in vacuo, the residue is taken up in methylene chloride, and the organic phase is washed with water. After drying over sodium sulphate, the solvent is removed and the residue which remains is taken up in cyclohexane. Undissolved starting material is removed and the solution is evaporated on a rotary evaporator. The oils which remain initially crystallize in a refrigerator.

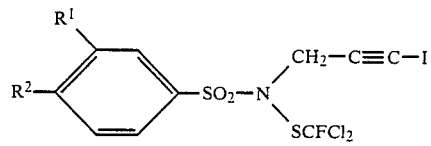

| Example | $R^1$ | $R^2$ | Melting point (°C.) |
|---|---|---|---|
| 30 | H | H | 82–84 |
| 31 | H | $CH_3$ | 106–108 |
| 32 | H | Cl | 99–101 |
| 33 | Cl | Cl | 81–83 |

USE EXAMPLES

Example 34

The minimum inhibitory concentrations (MIC) of active compounds according to the invention are determined in order to demonstrate their effectiveness against fungi:

Compounds according to the invention are added, in concentrations of 0.1 mg/l to 5,000 mg/l, to an agar prepared from beer wort and peptone. After the agar has solidified, it is contaminated with pure cultures of the test organisms listed in the table. The MIC is determined after storage for 2 weeks at 28° C. and 60 to 70% relative humidity. The MIC is the lowest concentration of active compound at which no growth at all takes place by the species of microbe used; it is indicated in the table below.

TABLE 1

| Test organisms | Comparison substance A* | Comparison substance B** | 1 | 2 | 4 | 6 | 8 | 14 | 17 | 19 | 21 | 22 | 20 | 24 | 28 | 25 | 27 | 26 |
|---|---|---|---|---|---|---|---|---|---|---|---|---|---|---|---|---|---|---|
| Alternaria tenuis | 10 | 10 | 20 | | 10 | 20 | 5 | 35 | | 100 | | | | | | | | |
| Aspergillus niger | 200 | 50 | 10 | 10 | 10 | 10 | 20 | 20 | 10 | 10 | 35 | 20 | 350 | 5 | 20 | 20 | 20 | 50 |
| Aureobasidium pullulans | 50 | 7.5 | 5 | | 3.5 | 10 | 5 | 5 | | 35 | | | | | | | | |
| Chaetomium globosum | 100 | 50 | 3.5 | <2 | 7.5 | 35 | 15 | 20 | 3.5 | <2 | 5 | 5 | 10 | 3.5 | 35 | 7.5 | 20 | 20 |
| Coniophora puteana | 2 | 7.5 | 0.5 | | 0.3 | 0.75 | 0.75 | 3.5 | | 7.5 | | | | | | | | |
| Lentinus tigrinus | 2 | 10 | 5 | | | 0.5 | 0.5 | 5 | 5 | 100 | | | | | | | | |
| Penicillium glaucum | 35 | 50 | 10 | 10 | 20 | 10 | 20 | 20 | 10 | 20 | 20 | 35 | 20 | 5 | 15 | 10 | 20 | 20 |
| Polyporus versicolor | 50 | 20 | 2 | | | 0.5 | 1 | 7.5 | 10 | 100 | | | | | | | | |
| Sclerophoma pityophila | 10 | 15 | 5 | | 3.5 | 7.5 | 5 | 3.5 | | 10 | | | | | | | | |

*Fluorfolpet
**Dichlofluanid

Example 35

(Action against slime organisms)

Substances according to the invention, dissolved in a little acetone, are used in concentrations of 0.1 to 100 mg/l in a particular case in Allen's nutrient solution (*Arch. Mikrobiol.*, 17, 34 to 53 (1952)), containing, in 4 l of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam. Shortly beforehand, the nutrient solution is infested with slime organisms (approx. $10^6$ microbes/ml) which have been isolated from circulating spinning water used in the production of polyamide. Nutrient solutions containing the minimum inhibitory concentration (MIC) or higher concentrations of active compound are still completely clear after being cultured for 3 weeks at room temperature, that is to say the considerable increase of microbes and formation of slime noticeable after 3 to 4 days in nutrient solutions free from active compounds does not take place.

TABLE 2

MIC values in mg/l when the substances indicated below act on slime organisms

| Active compound according to Example | MIC in mg/l |
|---|---|
| 1 | ≦2 |
| 2 | ≦2 |
| 3 | 2 to <5 |
| 4 | 2 to <5 |
| 6 | 1 to <2 |
| 8 | 1 to <2 |
| 12 | 1 to <5 |
| 14 | >2 to <5 |

Example 36

Determination of the limiting toxic values (kg/m³ of timber) of active compounds according to the invention for *Coniophora puteana* and *Polyporus versicolor* on pinewood and beechwood, respectively.

The limiting toxic values are determined by a method modelled on the method described by H. P. Sutter, *Int. Biodeterioration Bulletin*, 14 (3), 1978, pages 95 to 99.

For each test, freshly cut, thin pieces of cross-cut timber (dimensions 40×40 mm, thickness about 2 mm) are impregnated in vacuo with solutions of varying concentrations of active compounds. In each case one concentration of active compound is used to impregnate 15 timber samples simultaneously. 5 of these are in each case used at the same time for a mycological test.

The amount of active compound absorbed is determined from the retention of solvent (determined by weighing the small piece of timber before and after impregnation), the density of the timber and the concentration of the active compound in the residual impregnating solution.

Before the mycological test, the test specimens are sterilized with propylene oxide and in each case 1 test specimen is brought into contact in a Petri dish with the fully developed mycellium of the test fungus on malt extract agar. The toxicity limits are determined visually after 6 weeks at 21° to 23° C.

The toxicity limits (kg/cm³ of timber) for substances according to the invention are shown in the table below; the toxicity limits indicate the concentrations at which the timber is still attacked and at which the timber is no longer attacked.

TABLE 3

Toxicity Limits (kg/m³ of timber) of active compounds according to the invention for fungi which destroy timber

| Active compound according to Example | Coniophora puteana on pinewood | Polyporus versicolor on beechwood |
|---|---|---|
| Comparison substance* | 1.61–2.25 | 2.23–2.81 |
| 1 | 0.22–0.65 | 2.2–2.9 |
| 2 | 0.24–0.74 | 1.4–2.4 |
| 3 | 0.25–0.76 | 0.63–1.29 |
| 4 | 0.65–1.3 | 2.8–3.7 |
| 6 | 0.24 | <0.22 |
| 14 | 0.26–0.79 | 2.2–3.07 |
| 19 | 0.24–0.72 | 1.07–1.76 |

*Dichlofluanid

Comparison Example (Action in plant protection; in this regard see DE-AS (German Published Specification) No. 1,193,498).
Phytophthora test (tomatoes)/protective
Solvent: 4.7 parts by weight of acetone
Emulsifier: 0.3 parts by weight of an alkylaryl polyglycol ether An appropriate preparation of active compound is prepared by mixing 1 part by weight of active compound with the quantities of solvent and emulsifier indicated and diluting the concentrate with water to the desired concentration.

Testing for protective activity is carried out by spraying young plants with the preparation of active compound until they are dripping wet. When the spray coating has dried, the plants are inoculated with an aqueous spore suspension of *Phytophthora infestans*.

The plants are placed in an incubation cabin at 100% relative humidity and approx. 20° C.

Evaluation is carried out 30 days after inoculation.

TABLE (Comparison) Phytophthora test (tomatoes)/protective

| Active compound | % attack at an active compound concentration of 62 ppm | 10 ppm | |
|---|---|---|---|
| $CH_3$–N(–$CH_3$)–$SO_2$–N(–phenyl)–S–$CFCl_2$ | 19 | | disclosed in DE-AS (German Published Specification) 1,193,498, Example 2 and |
| $CH_3$–N(–$CH_3$)–$SO_2$–N(–p-tolyl)–S–$CFCl_2$ | 14 | | DE-AS (German Published Specification) 1,238,139, Examples 1 and 2 |
| 3-CH_3-4-Cl-C_6H_3–$SO_2$–N($CH_3$)–S–$CCl_2F$ | 67 | | disclosed in DE-AS (German Published Specification) 1,193,498, Example 4, columns 9 and 10 |
| 2-$NO_2$-C_6H_4–$SO_2$–N($CH_3$)–S–$CCl_2F$ | 82 | | |
| C_6H_5–$SO_2$–N($CH_3$)–S–$CCl_2F$ | 60 | | |
| 4-Cl-C_6H_4–$SO_2$–N($C_4H_9$)–S–$CCl_2F$ | 70 | | |

What is claimed is:

1. A method of protecting industrial materials against microbial attack comprising contacting an industrial material susceptible to microbial attack with an effective amount of an agent so as to prevent microbial attack, said agent comprising an N-sulphenylated benzenesulphonamide of the formula

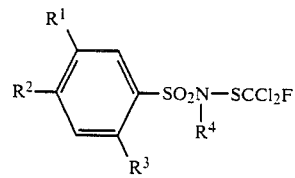

wherein
$R^1$, $R^2$ and $R^3$ independently of one another represent hydrogen, halogen, nitro, alkyl or halogenoalkyl and
$R^4$ denotes an unsubstituted or substituted saturated or unsaturated, aliphatic or cycloaliphatic radical, the aliphatic radicals being uninterrupted by hetero-atoms or being interrupted by one or more hetero-atoms, said industrial material being selected from the group consisting of adhesives, glues, paper, cardboard, textiles, leather, timber, plants, silicone rubbers and plastic articles.

2. An method according to claim 1, wherein $R^1$, $R^2$ and $R^3$ independently of one another represent hydrogen, chlorine, bromine, nitro, alkyl with 1 to 4 carbon atoms or halogenoalkyl having 1 to 4 carbon atoms and 1 to 5 halogens, and $R^4$ represents a radical selected from the group consisting of an alkyl radical having 1 to 6 carbon atoms, an alkenyl radical having 3 to 6 carbon atoms and an alkinyl radical having 3 to 6 carbon atoms, said radical being uninterrupted or being interrupted by one or more hetero-atoms, said hetero-atoms selected from the group consisting of oxygen and sulfur, said radical being unsubstituted or substituted by a halogen selected from the group consisting of chlorine and iodine, or $R^4$ represents cycloalkyl having 3 to 7 ring carbon atoms, said cycloalkyl being unsubstituted or substituted by one or more lower alkyl radical having 1 to 3 carbon atoms.

3. An method according to claim 1, wherein $R^1$ and $R^2$ independently of one another represent hydrogen, chlorine, nitro, methyl and trifluoromethyl, $R^3$ is hydrogen, $R^4$ is a radical selected from the group consisting of an alkyl radical having 1 to 6 carbon atoms, an alkenyl radical having 3 to 6 carbon atoms and an alkinyl radical having 3 to 6 carbon atoms, said radical being uninterrupted by hetero-atoms or said radical being interrupted by one or more hetero-atoms, starting from the second carbon atom, by a hetero-atom selected from the group consisting of oxygen and sulphur, said radicals being unsubstituted or substituted by iodine, or $R^4$ represents cycloalkyl having 3 to 7 ring carbon atoms which is unsubstituted or substituted by one or more methyl radicals.

4. An method according to claim 1, wherein the N-sulphenylated benzenesulphonamide is contained in an amount of 1 to 95% by weight.

5. An method according to claim 1, wherein the N-sulphenylated benzenesulphonamide is contained in an amount of 10 to 90% by weight.

6. A method according to claim 1, wherein 0.05 to 1.0% by weight of the N-sulphenylated benzenesulphonamide is employed, relative to the industrial material to be protected.

7. A method according to claim 1, wherein the industrial material is timber.

8. A method according to claim 1, wherein the industrial material is selected from the group consisting of paints and timber.

9. A method according to claim 1, wherein the material is protected against attack from a microorganism selected from the group consisting of bacteria, fungi, yeast, algae, slime and virus.

10. A method according to claim 1, wherein the material is protected against attack from a microorganism selected from the group consisting of mold fungi, fungi which discolor timber, fungi which destroys timber and slime organisms.

11. A method according to claim 1, wherein the material is protected against attack from a microorganism selected from the group consisting of alternaria, aspergillus, chaetomium, globosum, coniophora, lentinus, penicillium, polyporus, aureobasidium, sclerophoma and staphylococcus.

12. A method according to claim 11, wherein the microorganism is selected from the group consisting of *Alternaria tenuis, Aspergillus niger, Chaetomium globosum, Coniophora puteana, Lentinus tigrinus, Penicillium glaucum, Polyporus versicolor, Aureobasidium pullulans, Sclerophoma pityophila* and *Staphylococcus aureus*.

13. A method according to claim 1, wherein 0.001 to 5% by weight of the N-sulphenylated benzenesulphonamide is employed, relative to the industrial material to be protected.

* * * * *